United States Patent

Hermann et al.

[11] 4,322,426
[45] Mar. 30, 1982

[54] 17-SUBSTITUTED-6-DESOXY-7,8-DIHYDRO-6α-METHYLNOROXYMORPHONE NARCOTIC ANTAGONISTS

[75] Inventors: Edward C. Hermann, Newark; Kyu T. Lee; Melvyn J. Myers, both of Wilmington, all of Del.

[73] Assignee: E. I. Du Pont de Nemours and Company, Wilmington, Del.

[21] Appl. No.: 144,542

[22] Filed: Apr. 28, 1980

[51] Int. Cl.³ .................. A61K 31/485; C07D 489/08
[52] U.S. Cl. ........................................ 424/260; 546/44
[58] Field of Search .................... 546/44, 46; 424/260

[56] References Cited

U.S. PATENT DOCUMENTS

| | | | |
|---|---|---|---|
| 3,162,639 | 12/1964 | Fishman | 546/44 |
| 3,332,950 | 7/1967 | Blumberg et al. | 546/44 X |
| 3,814,768 | 6/1974 | Fishman | 546/44 |
| 4,089,855 | 5/1978 | Chatterjie et al. | 546/45 |

FOREIGN PATENT DOCUMENTS

| | | | |
|---|---|---|---|
| 913077 | 10/1972 | Canada | |
| 40-9268 | 5/1965 | Japan | 546/74 |
| 1012492 | 12/1965 | United Kingdom | 546/74 |

OTHER PUBLICATIONS von Braun et al., Chemische Berichte, 59, pp. 1081–1090, (1926).
Hahn, et al., J. Med. Chem. 18, pp. 259–262, (1975).
Horvath et al., Magy. Kem. Foly., 79, pp. 429–432, (1973).

*Primary Examiner*—Donald G. Daus
*Assistant Examiner*—Diana G. Rivers

[57] ABSTRACT

17-Substituted-6-desoxy-7,8-dihydro-6α-methylnoroxymorphone compounds corresponding to the formula

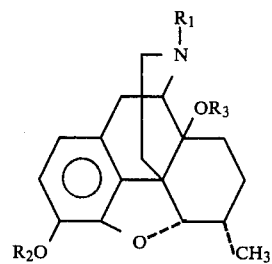

The compounds exhibit narcotic antagonistic properties.

8 Claims, No Drawings

17-SUBSTITUTED-6-DESOXY-7,8-DIHYDRO-6α-METHYLNOROXYMORPHONE NARCOTIC ANTAGONISTS

BACKGROUND OF THE INVENTION

This invention relates to novel narcotic antagonist compounds, compositions containing them and methods of using them.

The opioid analgesics (for example, morphine), although effective against severe pain, are not entirely free of risk. Since the drugs can produce euphoric effects in the user, they are often abused, and frequent use can lead to physical and/or psychological dependence. The addict who continuously uses the drug develops a significant tolerance to its euphorigenic effects and must constantly increase the dose to maintain a "high". Tolerance, however, is not absolute. Even in tolerant individuals, a dose exists which is capable of producing death from respiratory depression.

Certain drugs have been found which are useful for neutralizing or "antagonizing" the effects of narcotic drugs. These drugs, termed narcotic antagonists, have widely varying actions. Some antagonists, such as naloxone, are pure antagonists because they produce none of the effects associated with the opioid analgesics. Others, such as nalorphine or propiram, produce some of the effects of the opioid analgesics in addition to their powerful antagonistic actions.

The antagonists are extremely useful in treatment of patients suffering from opioid poisoning (i.e., overdose). Administration of narcotic antagonists can produce dramatic reversal of severe narcotic-induced respiratory depression. Often, a pure antagonist or one with very minimal agonistic activity is desired for this type of use; a mixed agonist-antagonist may only further decrease respiration that has been depressed by narcotic overdose.

On the other hand, it may in some instance be desired to reverse respiratory depression without also reversing the desirable analgetic effects of the opiate. In such cases, a mixed agonist-antagonist is especially useful.

The narcotic antagonists have other uses as well. They may, for example, be used to modify patterns of compulsive drug abuse. The antagonists act to attenuate or even entirely block the effects of the opioids and thus interfere with the reinforcing or satisfying properties of the drugs. Some mixed agonist-antagonists may have yet a further use as non-addictive analgesics.

Quite a few narcotic antagonists are known in the art. U.S. Pat. No. 3,332,950 to Blumberg et al. (1967) teaches that compounds of the following formula are useful as narcotic antagonists:

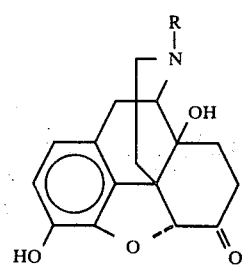

where R is 3'-methyl-2'-butenyl, cyclopropylmethyl, or cyclobutylmethyl.

Compounds of the formula

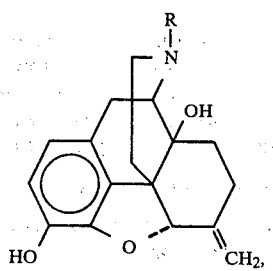

where R is allyl or cyclopropylmethyl, are taught to have antagonistic activity in E. F. Hahn, et al., *J. Med. Chem.* 18, 259 (1975).

A process for preparing compounds of the formula

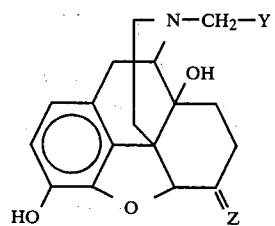

where Y is cyclobutyl or cyclopropyl and Z is

or O is disclosed in Canadian Pat. No. 913,077, dated Oct. 24, 1972.

G. Horvath et al., *Magy. Kem. Foly.* 79, 429 (1973), discloses narcotic analgetics without antagonist activity of the formula

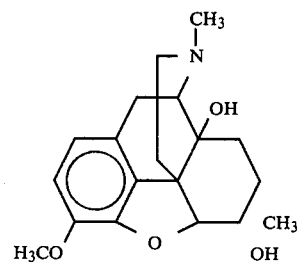

U.S. Pat. No. 3,162,639 to Fishman (1964) teaches compounds of the formula

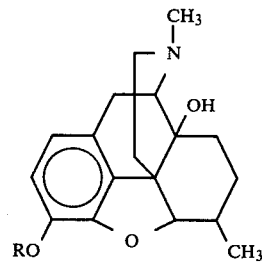

where R is H or CH$_3$. These compounds are disclosed to be analgesics and are not taught to have antagonistic activity.

With the ever-increasing incidence of drug abuse in our society, the need for new narcotic antagonists is clear. New antagonists which are safer and longer-acting than those known in the art or which exhibit new degrees of effectiveness are especially needed.

SUMMARY OF THE INVENTION

According to this invention, new compounds which are useful as narcotic antagonists have been found. These compounds correspond to the general formula

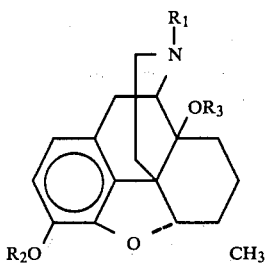

wherein

R$_1$ is selected from C$_3$-C$_7$ alkyl,

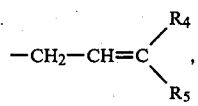

propargyl, C$_3$-C$_6$ cycloalkylmethyl, tetrahydrofurylmethyl, furylmethyl, thienylmethyl, and

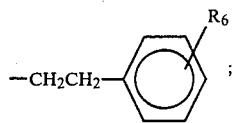

R$_2$ is selected from —H, methyl and C$_2$-C$_4$ acyl;
R$_3$ is selected from H and C$_2$-C$_4$ acyl;
R$_4$, R$_5$ and R$_6$ are independently —H or CH$_3$; and pharmaceutically suitable acid addition salts thereof.

Preferred for their greater narcotic antagonistic effectiveness are those compounds in which independently R$_1$ is C$_3$-C$_6$ cycloalkylmethyl and R$_2$ and R$_3$ are —H.

More preferred for their greater narcotic antagonistic effectiveness are those preferred compounds in which R$_1$ is cyclopropylmethyl or cyclobutylmethyl.

The most preferred compound is 17-cyclopropylmethyl-6-desoxy-7,8-dihydro-6α-methylnoroxymorphone.

This invention further includes pharmaceutical compositions containing the above-described compounds and methods of using said compounds to antagonize the effects of opiate analgesics in mammals.

Synthesis

The compounds of this invention may be synthesized by either of two reaction sequences.

The first sequence is illustrated as follows:

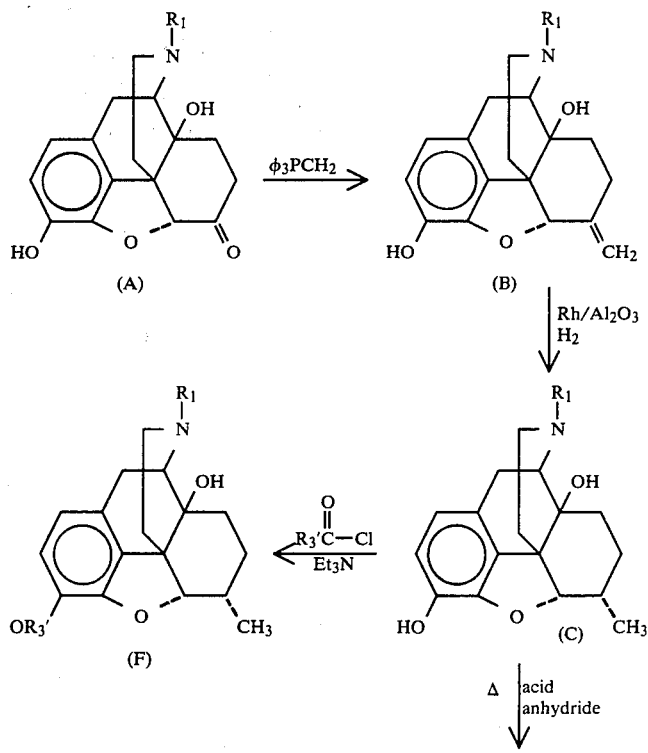

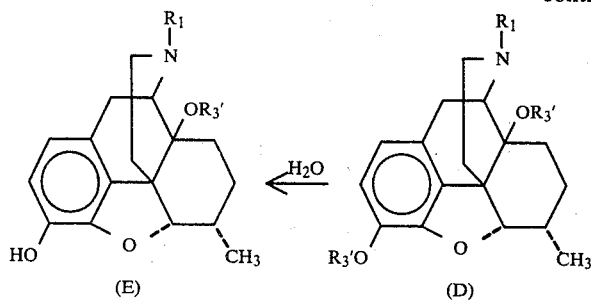

where $R_3' = C_2-C_4$ acyl.

In the first step of this process, a compound of Formula A, wherein $R_1$ is as previously defined, is reacted with methylene triphenylphosphorane using the procedure outlined in E. F. Hahn et al., *J. Med. Chem.*, 18, 259 (1975), the disclosure of which is herein incorporated by reference. The 6-methylene compound produced by this reaction, represented by Formula B, is isolated and then catalytically hydrogenated to yield the 6-methyl compound of Formula C. Suitable hydrogenation catalysts include rhodium on alumina and palladium or platinum on carbon. The solvent, either an alcohol such as ethanol or acetic acid, is purged with nitrogen to remove all dissolved oxygen. The reaction is run under a hydrogen pressure of approximately 50 lbs psi.

The compounds thus prepared are the compounds of this invention wherein both $R_2$ and $R_3$ are hydrogen. To prepare compounds wherein either $R_2$ or $R_3$, or both, are $C_2-C_4$ acyl, the compounds of Formula C are reacted with the appropriate acid anhydride in pyridine to produce the 3,14-diacyl compounds of Formula D. Partial hydrolysis of the diacyl compounds yields the 14-acyl compounds of Formula E. To prepare compounds wherein $R_2$ is $C_2-C_4$ acyl and $R_3$ is H, the compounds of Formula C are reacted with one equivalent of an acyl chloride in the presence of triethylamine.

The compounds of Formula A used as starting materials for the above-defined process are prepared according to procedures taught in Canadian Pat. No. 913,077, the disclosure of which is hereby incorporated by reference.

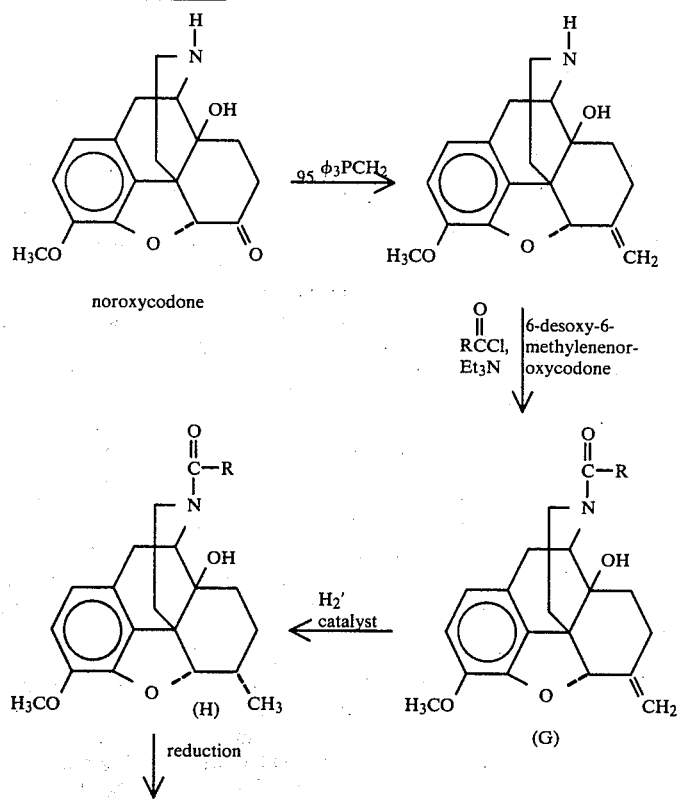

-continued

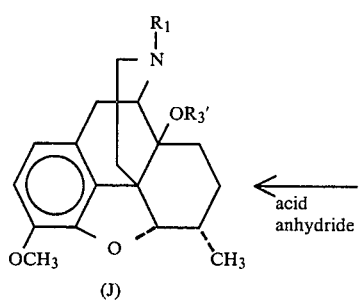
(J)

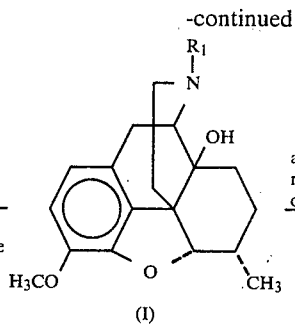
(I)

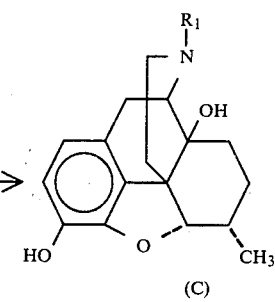
(C)

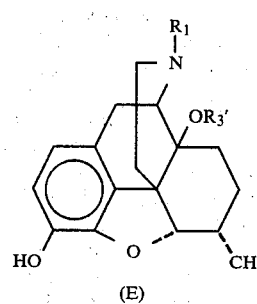
(E)

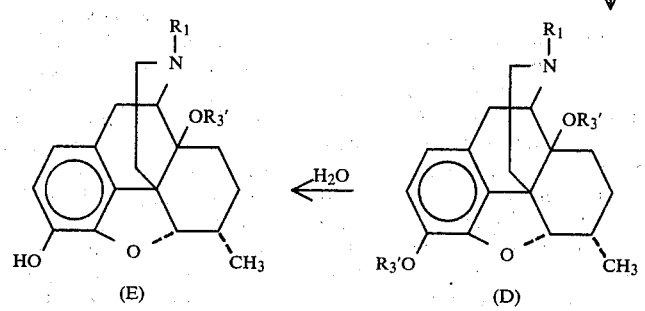
(D)

where $R_3' = C_2-C_4$ acyl.

In a second method for preparing the claimed compounds, noroxycodone is reacted with methylene triphenylphosphorane to yield 6-desoxy-6-methylenenoroxycodone. The methylene triphenylphosphorane is generated in situ by the reaction of methyl triphenylphosphonium bromide with a suitable base. Suitable bases include alkali metal hydrides, such as sodium or potassium hydride, and alkali metal alkoxides, such as potassium t-butoxide. The reaction is run at a temperature of about 65° C. for a period of about 6–48 hours. Suitable solvents include tetrahydrofuran, dimethylsulfoxide and dialkyl ethers such as glyme and diglyme.

The 6-desoxy-6-methylenenoroxycodone is isolated and converted to the amide (Formula G) by reaction with the appropriate acid chloride in the presence of a base such as triethylamine. The reactants are combined in an aprotic solvent such as methylene chloride or chloroform. Temperature is not critical and may range from 0° C. to the boiling point of the solvent.

As in Method I, the isolated amide of Formula G is reduced to the 6α-methyl compound of Formula H by hydrogenation in the presence of a catalyst such as rhodium or alumina. The resulting compound is then reduced to yield the 3-methoxy compounds of this invention represented by Formula I. This final reduction is carried out by reaction of the compound of Formula H with lithium aluminum hydride. Other suitable reducing agents are tetrahydrofuran-borane and sodium bis-2-(methoxyethoxy)aluminum hydride. An aprotic solvent is used, for example, ether, tetrahydrofuran, glyme or diglyme. The reaction may be run at a temperature of from room temperature to the reflux temperature of the solvent.

The methoxy compounds of Formula I may be acylated to yield the compounds of Formula J by reaction with the appropriate acid anhydride. Alternatively, the compounds of Formula I may be demethylated to yield 3-ol compounds of this invention as represented by Formula C. The compound of Formula I is demethylated with an alkanethiol and an alkali metal hydride or alkoxide in dimethylformamide or dimethylsulfoxide. The reaction is run at a temperature of about 50°–150° C. for approximately one to three hours.

As in Method I, the resulting compounds may be acylated to form the compounds of this invention represented by Formulas D and E.

The noroxycodone used as starting material for Method II is prepared from oxycodone by the following steps:

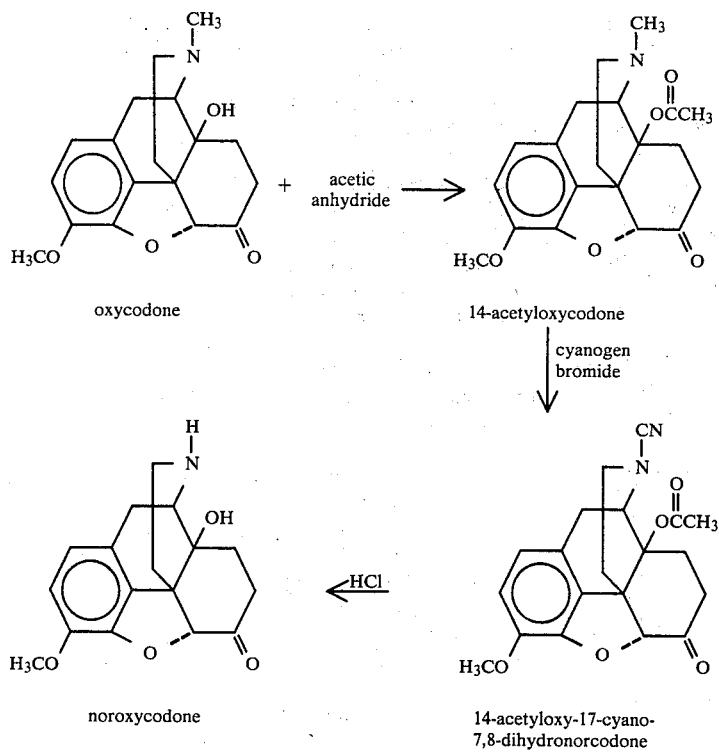

Oxycodone is refluxed with acetic anhydride to yield 14-acetyloxycodone. This product is reacted with cyanogen bromide to yield 14-acetyloxy-17-cyano-7,8-dihydronorcodone which is in turn converted to noroxycodone by reaction with hydrogen chloride. The oxycodone starting material is prepared according to M. Freund and E. Speyer, J. für Praktische Chemie, 94, 135–137 (1916), the disclosure of which is hereby incorporated by reference.

The compounds of this invention are unique in that the stereochemical configuration of the 6-methyl is identical to that of the 6-hydroxy in natural morphine and codeine. The reduction of the 6-methylene to the 6-methyl compound may theoretically produce two isomers, α- and β-.

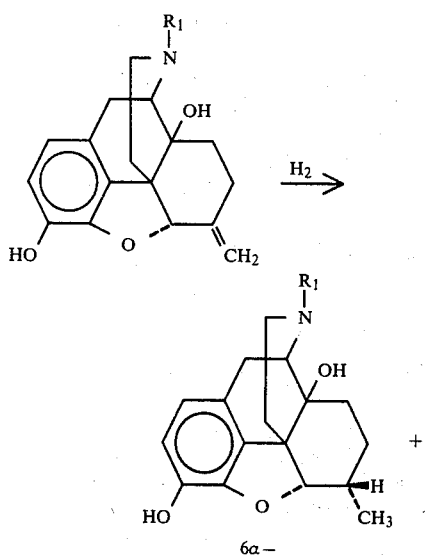

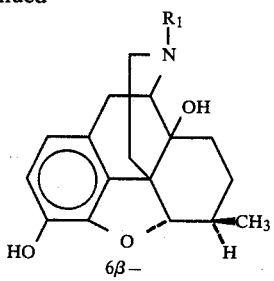

The catalytic reduction described above, however, yields almost pure 6α-methyl, with less than 2% 6β-methyl. In natural morphine and codeine, the 6-hydroxy is in the α-configuration.

Pharmaceutically suitable acid addition salts of the compounds of this invention promote water solubility and include those made with physiologically acceptable acids that are known in the art; such salts include hydrochloride, sulfate, nitrate, phosphate, citrate, tartrate and maleate.

The compounds of this invention and methods of preparing them are illustrated in the following examples. Unless indicated to the contrary, all temperatures are in degrees Centigrade.

EXAMPLE 1

6-Desoxy-6α-methylnaltrexone a. 14.4 g of 50% sodium hydride was added slowly in portions to 107 g of methyltriphenylphosphonium bromide in 100 ml of dimethylsulfoxide under nitrogen. The mixture was stirred one hour and then 10.2 g of naltrexone was added. The mixture was heated in an oil bath at 55°–60° for 40 hours with mechinical stirring. To the cooled mixture, 150 ml of saturated ammonium chloride was added dropwise. The reaction solution was then extracted 5 times with 300 ml of ether. The combined ether solution was washed 3 times with water, twice with 600 ml of saturated sodium chloride solution, and dried with sodium sulfate. The drying agent was filtered off and the ether evaporated to yield an oil. Product was extracted out of the oil by trituration with 1 liter of 1 N HCl. The HCl solution was washed with 200 ml of chloroform, 500 ml of ether, and basified to pH9 with dilute sodium hydroxide. The precipitated white crystalline solid was filtered off, washed with water and dried in a vacuum oven at 70° to yield 6.3 g, m.p. 177°–185°. This was dissolved in 60 ml of boiling ethyl acetate. Boiling reduced the volume to 30 ml. This was allowed to crystallize overnight. The solid was filtered, washed with ethyl acetate and dried at 70° under vacuum to yield 5.1 g of 6-desoxy-5-methylenenaltrexone (m.p. 187°–189°).

b. A 2.9 g portion of 6-desoxy-6-methylenenaltrexone, was dissolved in 250 ml of ethanol. After bubbling nitrogen through the solution for 30 minutes to displace oxygen, 0.3 g of 5% rhodium on alumina was added and the solution was hydrogenated on a Paar apparatus at 50 lbs. psi until take-up of hydrogen ceased. The resulting solution was filtered to remove the rhodium catalyst, after which the ethanol was evaporated. The remaining solid was recrystallized from ethyl acetate to produce a final yield of 2.0 g 6-desoxy-6α-methylnaltrexone (m.p. 160°–162°).

EXAMPLE 2

6-Desoxy-6α-methyl-17-cyclopentylmethylnoroxycodone a. 315 g of oxycodone was refluxed with 1600 ml of acetic anhydride for one hour. After cooling the mixture to 50°, acetic anhydride and acetic acid were removed with the rotary evaporator. The solid remaining was dissolved in water and the solution was basified to pH9 with ammonia. The precipitated product was filtered off, washed with water and vacuum dried to yield 357 g of 14-acetyloxycodone (m.p. 215°–216°).

357 g of 14-acetyloxycodone and 160 g of dried cyanogen bromide were refluxed in 2.5 l of chloroform for 10 hours. The chloroform was evaporated, and 500 ml of ethanol was added to the residue. The mixture was cooled to 0°, and the solid was filtered off and washed with cold ethanol to yield 295 g of 14-acetyloxy-17-cyano-7,8-dihydronorcodone (m.p. 249° with decomposition).

295 g of 14-acetyloxy-17-cyano-7,8-dihydronorcodone was refluxed in 2.5 l of 3 N HCl for 8 hours. Upon cooling the product crystallized out as the hydrochloride salt. This was filtered off and gave 221 g. This salt was dissolved in 3 l of water and made basic with sodium hydroxide. The product was filtered off, washed with water and dried at 100° in a vacuum oven. The cooled product was triturated with 1 l of ether. Filtering and drying yielded 199 g of noroxycodone (m.p. 169° froth, 310° decomposition).

b. To 14.0 g of potassium tert-butoxide and 250 ml of tetrahydrofuran, a 47.3 g portion of methyl triphenylphosphonium bromide was added under nitrogen. The mixture was stirred one hour at ambient temperature. Next, 7.5 g of noroxycodone was added and the mixture was refluxed for 48 hours. The reaction mixture was cooled and 100 ml of saturated ammonium chloride was added dropwise, followed by 250 ml of 1 N hydrochloric acid. The product was partitioned into the acid layer, which was washed two times with ether and once with chloroform. The acid layer was made basic with sodium hydroxide, and the precipitated product was filtered off and washed with water to yield 6.2 g of 6-desoxy-6-methylenenoroxycodone (m.p. 121°–123°).

c. A 12.0 g (0.04 mole) portion of 6-desoxy-6-methylenenoroxycodone was dissolved in 100 ml of methylene chloride containing 20.2 g (0.2 mole) of triethylamine. The solution was stirred under a nitrogen atmosphere, and a solution of 11.92 g (0.09 mole) of cyclopentanecarboxylic acid chloride in 20 ml of methylene chloride was added dropwise. The temperature of the solution was maintained below 35°. After completion of the acid chloride addition, the mixture was stirred for two hours. Next, the mixture was partitioned with water and washed twice with 50 ml of 5% sodium carbonate, twice with 50 ml of 0.5 N HCl and once with 50 ml of water. The resulting solution was dried over sodium sulfate, filtered and evaporated under reduced pressure to yield 15.8 g of a colorless oil, 6-desoxy-6-methylene-17-cyclopentylcarbonylnoroxycodone. A 15.8 g portion of the 6-desoxy-6-methylene-17-cyclopentylcarbonylnoroxycodone was dissolved in 250 ml of ethanol. After bubbling nitrogen through the solution for 30 minutes to displace oxygen, 1.5 g of 5% rhodium on alumina catalyst was added, and the mixture was hydrogenated on a Paar apparatus at 50 lbs psi until hydrogen take-up ceased. The resulting mixture was filtered to remove the rhodium catalyst, and the ethanol was evaporated to yield 15.8 g of 6-desoxy-6α-methyl-17-cyclopentylcarbonylnoroxycodone.

A solution of 15.8 g (0.04 mole) of the 6-desoxy-6α-methyl-17-cyclopentylcarbonylnoroxycodone in 75 ml of tetrahydrofuran was added dropwise to 15 g (0.4 mole) of lithium aluminum hydride in 100 ml of tetrahydrofuran at ambient temperature. After being refluxed for 6 hours, the mixture was decomposed by the careful dropwise addition of water. The precipitated lithium aluminate was filtered off and washed with methylene chloride. The remaining solution was evaporated under reduced pressure to yield 6-desoxy-6α-methyl-17-cyclopentylmethylnoroxycodone. The crude product was recrystallized from ethanol to yield 10.4 g, m.p. 114°–116°.

The following compounds may also be prepared by the procedure outlined in Example 2:
6-Desoxy-6α-methyl-17-cyclohexylmethylnoroxycodone
6-Desoxy-6α-methyl-17-furylmethylnoroxycodone
6-Desoxy-6α-methyl-17-tetrahydrofurylmethylnoroxycodone, m.p. 100°–1°
6-Desoxy-6α-methyl-17-thienylmethylnoroxycodone
6-Desoxy-6α-methyl-17-(4'-methylphenethyl)noroxycodone
6-Desoxy-6α-methyl-17-butylnoroxycodone
6-Desoxy-6α-methyl-17-pentylnoroxycodone
6-Desoxy-6α-methyl-17-hexylnoroxycodone

EXAMPLE 3

6-Desoxy-6α-methyl-17-cyclopentylmethylnoroxymorphone hydrochloride

Nitrogen was bubbled through a 60 ml portion of dimethylformamide (DMF) for 30 minutes to remove dissolved oxygen. Next, 3.0 g of 6-desoxy-6α-methyl-17-cyclopentylmethylnoroxycodone, prepared as in Example 2, was added to the DMF. The solution was stirred under a nitrogen atmosphere while 3.0 g of potassium t-butoxide and 3.0 ml of propanethiol were added. After being heated in an oil bath at 130° for three hours, the mixture was cooled in an ice bath and 3.0 ml of acetic acid were added to it. A solid was formed by evaporating the mixture under vacuum (0.1 mm Hg). 10 ml of 3 N HCl were added to the solid to produce a clear solution. In a few minutes the hydrochloride salt of 6-desoxy-6α-methyl-17-cyclopentylmethylnoroxymorphone crystallized out of the solution. The crude product, in a yield of 2.4 g, had a melting point of 270°–272°. After recrystallization from ethanol, the pure product, in a yield of 2.0 g, had a melting point of 272°.

The following compounds may also be prepared by the procedure in Example 3:

6-Desoxy-6α-methyl-17-cyclohexylmethylnoroxymorphone.HCl, m.p. 280°
6-Desoxy-6α-methyl-17-furylmethylnoroxymorphone.HCl, m.p. 210°–11°
6-Desoxy-6α-methyl-17-tetrahydrofurylmethylnoroxymorphone.HCl, m.p. 218°–20°
6-Desoxy-6α-methyl-17-thienylmethylnoroxymorphone.HCl, m.p. 215°–17°
6-Desoxy-6α-methyl-17-(4'-methylphenethyl)noroxymorphone.HCl, m.p. 272°
6-Desoxy-6α-methyl-17-butylnoroxymorphone.HCl, m.p. 229°–31°
6-Desoxy-6α-methyl-17-pentylnoroxymorphone.HCl, m.p. 236°–7°
6-Desoxy-6α-methyl-17-hexylnoroxymorphone.HCl, m.p. 245°–6°

Utility

Compounds of this invention were tested for analgesic and antagonistic activity. The tests and results are as follows.

ANALGESIC TESTING PROCEDURES

A standard procedure for detecting and comparing the analgesic activity of a series of compounds for which there is good correlation with human efficacy is the standard phenylquinone writhing test (PQW) modified from Siegmund, et al., *Proc. Soc. Exp. Biol. Med.*, 95, 729 (1957). A test compound suspended in 1% methocellulose was given orally to fasted (17–21 hours) female white mice, 5–20 animals per double blind test. Aqueous (0.1% phenyl-p-benzoquinone) phenylquinone was injected intraperitoneally at 24 minutes later using 0.20 ml per mouse. Commencing at 30 minutes after the oral administration of the test compound, the mice were observed for 10 minutes for a characteristic stretching or writhing syndrome which is indicative of pain induced by phenylquinone. The effective analgesic dose for 50% of the mice ($ED_{50}$) was calculated by the moving average method of Thompson, W. R., *Bact. Rev.*, 11, 115–145 (1947).

The data obtained from the phenylquinone writhing test are in the following table. These data show that most of the compounds of this invention exhibit effectively no analgesic activity; several of the compounds, notably Compounds 6 and 7, are weakly analgetic.

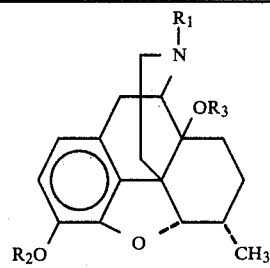

| Compound | $R_1$ | $R_2$ | $R_3$ | Oral PQW | Intraperitoneal Anti-Straub Tail |
|---|---|---|---|---|---|
| 1 | —CH$_2$—cyclopropyl | H | H | >135.<br>103.<br>91. | 0.05<br>0.018 |
| 2 | —CH$_2$—cyclobutyl | CH$_3$ | H | 112. | 5.0 |
| 3 | —CH$_2$—cyclobutyl | H | H | >135. | 0.34 |
| 4 | —CH$_2$—cyclopentyl | CH$_3$ | H | >135.0 | 14.5 |
| 5 | —CH$_2$—cyclopentyl | H | H | >135.0 | 2.1 |
| 6 | —CH$_2$—(tetrahydrofuryl) | CH$_3$ | H | 36. | 6.0 |
| 7 | —CH$_2$—(tetrahydrofuryl) | H | H | 65. | 0.53 |
| Morphine | | | | 3.0 | — |

-continued

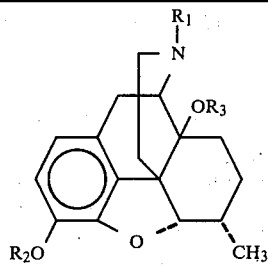

| Compound | $R_1$ | $R_2$ | $R_3$ | EFFECT ED50 (mg) Oral-PQW | Intraperitoneal Anti-Straub Tail |
|---|---|---|---|---|---|
| Naloxone | | | | — | 0.012 |

Antagonistic Testing Procedure

Narcotic analgesics produce in mice an erection and arching of the tail (90° or more) which is referable to spinal cord stimulation. This Straub tail reaction is not produced by other analgesics, including the narcotic antagonists.

Known narcotic antagonists such as naloxone and nalorphine prevent the induction of Straub tail in mice by a highly addicting agonist such as morphine [H. Blumberg. H. B. Dayton and P. S. Wolf, *The Pharmacologist*, 10, 189 (1968)]. This property is the basis of a mouse test for narcotic antagonists.

Female $CF_1S$ mice (fasted 17–21 hrs.), 5 per dose, were injected orally or subcutaneously (loose skin inside hind limb) with test drug at 0.67, 2, 6, 18, 54 and 162 mg/kg or other appropriate doses in 0.20 ml 1% Methocel ® per mouse. Ten minutes later, 40 mg/kg (base weight) of morphine sulfate in 0.20 ml 1% Methocel ® per mouse was given subcutaneously (nape of neck). The mice were observed continuously for the next 20 minutes after the first mouse of a group of 30 had received morphine. Prevention of a 90° Straub tail during this observation period was taken as indication of narcotic antagonist ability.

The data in the preceding table show that all of the compounds tested exhibit narcotic antagonism capability. Indeed, Compound No. 1 has almost the antagonistic activity of naloxone, the standard to which narcotic antagonists are compared. Thus, the compounds of this invention are useful for reversing the effects of opioid drugs in mammals. These effects include autonomic, endocrine, analgesic and respiratory depressant effects.

Dosage Forms

The compounds of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and the extent of symptoms, kind of concurrent treatment, frequency of treatment, and the effect desired. Usually a daily dosage of active ingredient can be about 0.02 to 50 milligrams per kilogram of body weight. Ordinarily 0.05 to 20 and preferably 0.1 to 10 milligrams per kilogram per day given in divided doses 4 to 6 times a day or in sustained release form is effective to obtain desired results.

Dosage forms (compositions) suitable for internal administration contain from about 1.0 milligram to about 50 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl or propyl-paraben and chlorobutanol.

Useful pharmaceutical dosage-forms for administration of the compounds of this invention can be illustrated as follows:

Hard Gelatin Capsules

Hard gelatin capsules can be prepared by filling standard two-piece hard gelatin capsules with the following mixture using conventional encapsulating equipment.

| Active ingredient | 50 mg. |
|---|---|
| Lactose | 234 mg. |
| Talc | 10 mg. |
| Magnesium stearate | 6 mg. |

Soft Gelatin Capsules

A mixture of 50 mg. active drug in Polysorbate 80-150 mg; Glycerin-15 mg; and Purified Water-10 mg. is prepared and injected by means of a positive displacement pump in gelatin to form gelatin capsules. A soft gelatin capsule will contain 50 mg active ingredient. The capsules are washed in petroleum ether and dried.

Tablets

Tablets can be prepared by conventional procedures so that each tablet will contain:

| Active ingredient | 50 mg. |
|---|---|
| Corn Starch | 25 mg. |
| Microcrystalline Cellulose | 100 mg. |
| Lactose | 320 mg. |
| Magnesium Stearate | 5 mg. |

Appropriate coatings may be applied to increase palatability or delay absorption.

Injectable

A parenteral composition suitable for administration by injection is prepared so that each 1 ml. contains:

| Active ingredient | 0.5 mg. |
|---|---|
| Sodium Chloride | 8.6 mg. |
| Methyl paraben | 1.8 mg. |
| Propylparaben | 0.2 mg. |
| Water for Injection | q.s. |

A wide variety of other pharmaceutical carriers, diluents and additives can be used. These are described in *Remington's Pharmaceutical Sciences*, E. W. Martin, a well-known reference in this field.

We claim:

1. A compound of the formula

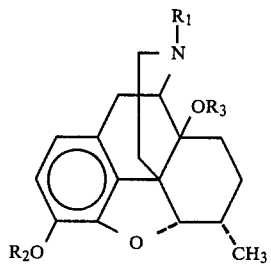

wherein
$R_1$ is selected from $C_3$-$C_7$ alkyl,

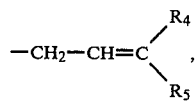

propargyl, $C_3$-$C_6$ cycloalkylmethyl, tetrahydrofurylmethyl, furylmethyl, thienylmethyl, and

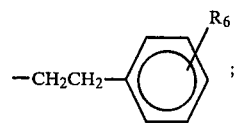

$R_2$ is selected from —H, methyl and $C_2$-$C_4$ acyl;
$R_3$ is selected from —H and $C_2$-$C_4$ acyl;
$R_4$, $R_5$ and $R_6$ are independently —H or $CH_3$;
and pharmaceutically suitable acid addition salts thereof.

2. A compound of claim 1 in which $R_1$ is $C_3$-$C_6$ cycloalkylmethyl.

3. A compound of claim 2 in which $R_1$ is cyclopropylmethyl or cyclobutylmethyl.

4. A compound of claim 1 in which $R_2$ and $R_3$ are —H.

5. A compound of claim 1 in which $R_1$ is cyclopropylmethyl or cyclobutylmethyl and $R_2$ and $R_3$ are —H.

6. The compound of claim 1 which is 17-cyclopropylmethyl-6-desoxy-7,8-dihydro-6α-noroxymorphone.

7. A composition useful for antagonizing the effects of opioid analgesics in mammals comprising a pharmaceutically suitable carrier and an antagonistically effective amount of a compound of any of claims 1-6.

8. A method for antagonizing the effects of opioid analgesics in mammals comprising administering to the mammal an antagonistically effective amount of a compound of any of claims 1-6.

* * * * *

UNITED STATES PATENT OFFICE
CERTIFICATE OF CORRECTION

PATENT NO. : 4,322,426  
DATED : March 30, 1982  
INVENTOR(S) : Edward Charles Hermann, Kyu T. Lee and Melvyn J. Myers Page 1 of 2

It is certified that error appears in the above-identified patent and that said Letters Patent are hereby corrected as shown below:

Column 2, lines 42-53, the correct figure is:

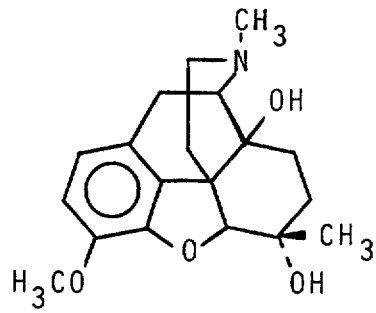

Column 3, lines 14-25, the correct figure is:

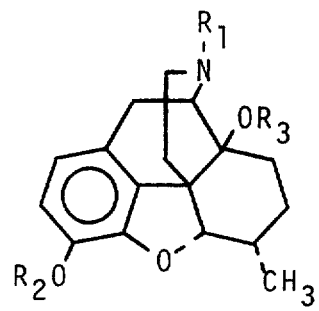

UNITED STATES PATENT OFFICE
CERTIFICATE OF CORRECTION

PATENT NO. : 4,322,426          Page 2 of 2

DATED : March 30, 1982

INVENTOR(S) : Edward Charles Hermann, Kyu T. Lee and Melvyn J. Myers

It is certified that error appears in the above-identified patent and that said Letters Patent are hereby corrected as shown below:

Col. 18 lines 43-44
Claim 6 should read:

6. The compound of Claim 1 which is 17-cyclopropyl-methyl-6-desoxy-7,8-dihydro-6α-methylnoroxymorphone.

Signed and Sealed this

Twenty-second Day of February 1983

[SEAL]

Attest:

GERALD J. MOSSINGHOFF

Attesting Officer     Commissioner of Patents and Trademarks